United States Patent
Duan et al.

(10) Patent No.: US 11,819,320 B2
(45) Date of Patent: Nov. 21, 2023

(54) METHOD AND SYSTEM FOR DETERMINING ORIENTATION OF CAPSULE ENDOSCOPE

(71) Applicants: Ankon Medical Technologies (Shanghai) Co., LTD., Shanghai (CN); Anx IP Holding PTE. LTD., Singapore (SG)

(72) Inventors: Xiaodong Duan, Pleasanton, CA (US); Qingqing Wang, Shanghai (CN)

(73) Assignees: Ankon Medical Technologies (Shanghai) Co., LTD, Shanghai (CN); ANX IP HOLDING PTE. LTD., Singapore (SG)

( * ) Notice: Subject to any disclaimer, the term of this patent is extended or adjusted under 35 U.S.C. 154(b) by 107 days.

(21) Appl. No.: 17/199,360

(22) Filed: Mar. 11, 2021

(65) Prior Publication Data
US 2021/0282661 A1    Sep. 16, 2021

(30) Foreign Application Priority Data
Mar. 11, 2020    (CN) .......................... 202010166284.7

(51) Int. Cl.
  *A61B 1/00*    (2006.01)
  *A61B 5/06*    (2006.01)
  *G16H 20/40*   (2018.01)
  *A61B 1/04*    (2006.01)

(52) U.S. Cl.
  CPC .......... *A61B 5/062* (2013.01); *A61B 1/00009* (2013.01); *A61B 1/041* (2013.01); *G16H 20/40* (2018.01)

(58) Field of Classification Search
  CPC ..... A61B 5/062; A61B 1/00009; A61B 1/041; A61B 1/00006; A61B 1/00158; A61B 1/045; A61B 5/002; A61B 5/0077; A61B 5/4238; A61B 2562/0219; A61B 5/6861; A61B 2562/0223; A61B 1/00131; G16H 20/40; G16H 40/63
  See application file for complete search history.

(56) References Cited

U.S. PATENT DOCUMENTS

| | | | |
|---|---|---|---|
| 9,211,084 B2 * | 12/2015 | Uchiyama | A61B 34/73 |
| 2007/0221233 A1 * | 9/2007 | Kawano | A61B 1/041 |
| | | | 128/899 |
| 2013/0317357 A1 * | 11/2013 | Iddan | A61B 1/00158 |
| | | | 600/424 |

(Continued)

*Primary Examiner* — Anh Tuan T Nguyen
*Assistant Examiner* — Sung Ham
(74) *Attorney, Agent, or Firm* — Treasure IP Group, LLC

(57) ABSTRACT

The present invention discloses a method and system for determining orientation of a capsule endoscope. An external magnetic field is provided outside the capsule endoscope, and an internal magnetic field is provided inside the capsule endoscope. Magnetic field data is obtained according to the external magnetic field and the internal magnetic field, and acceleration data of the capsule endoscope is obtained. When the polarization direction of the external magnetic field is horizontal, the orientation information of the capsule endoscope is obtained according to the acceleration data. When the polarization direction of the external magnetic field is non-horizontal, the orientation information of the capsule endoscope is obtained according to the acceleration data and the magnetic field data.

13 Claims, 4 Drawing Sheets

(56) References Cited

U.S. PATENT DOCUMENTS

| | | | |
|---|---|---|---|
| 2014/0148643 A1* | 5/2014 | Kawano | A61B 5/704 600/102 |
| 2014/0155709 A1* | 6/2014 | Ikai | A61B 1/00158 600/302 |
| 2015/0018615 A1* | 1/2015 | Duan | A61B 1/00006 600/109 |
| 2015/0342501 A1* | 12/2015 | Di Natali | A61B 5/07 600/424 |
| 2016/0135668 A1* | 5/2016 | Gat | A61B 1/00158 600/118 |
| 2018/0084976 A1* | 3/2018 | Duan | A61B 1/00158 |
| 2022/0354349 A1* | 11/2022 | Schostek | A61B 90/50 |

* cited by examiner

METHOD AND SYSTEM FOR DETERMINING ORIENTATION OF CAPSULE ENDOSCOPE

CROSS-REFERENCE OF RELATED APPLICATIONS

The application claims priority to Chinese Patent Application No. 202010166284.7 filed on Mar. 11, 2020, the contents of which are incorporated by reference herein.

FIELD OF INVENTION

The present invention relates to the field of medical technology, and more particularly to a method and system for determining orientation of a capsule endoscope.

BACKGROUND

A capsule endoscope is a capsule-shaped endoscope that integrates a battery, an imaging device, a communication device, etc. It can be swallowed by a subject to take images of tissues and organs in body lumen of the subject and transmit the images to an external display device. Compared with a traditional endoscope, the capsule endoscope has many advantages such as not causing pain, trauma and cross infection to the subject, not affecting normal activities of the subject, and high diagnostic rate. Therefore, capsule endoscope has been widely used in medical field.

In the actual use of a capsule endoscope, it is necessary to determine the location and orientation of the capsule endoscope, so as to assist the operator to control the capsule endoscope and adjust its orientation and path. In the prior art, in order to acquire the orientation information of a capsule endoscope, it is usually required to use at least a magnetic field sensor to determine the orientation of the capsule endoscope and thereby acquire corresponding information. Specifically, a magnetic field sensor is integrated inside the capsule endoscope, and an external magnetic field is provided at a location corresponding to the capsule endoscope outside the body of the subject. During determining the orientation of the capsule endoscope, the direction of the external magnetic field needs to be kept horizontal. However, because of the need to change the orientation of the capsule endoscope during an examination, it is difficult to keep the external magnetic field horizontal, which in turn leads to a large error between the acquired orientation information and the actual one of the capsule endoscope.

Therefore, a further improvement of the method and system for determining orientation of the capsule endoscope is expected to achieve an accurate orientation.

SUMMARY OF THE INVENTION

In order to solve the above-mentioned problems, the present invention provides a method and system for determining orientation of a capsule endoscope, so as to achieve an accurate orientation of the capsule endoscope.

According to one aspect of the present invention, a method for determining orientation of a capsule endoscope is provided. The method comprises: providing an external magnetic field outside the capsule endoscope; providing an internal magnetic field inside the capsule endoscope; obtaining magnetic field data according to the external magnetic field and the internal magnetic field; obtaining acceleration data of the capsule endoscope; and obtaining the orientation information of the capsule endoscope according to the acceleration data when the polarization direction of the external magnetic field is horizontal, and obtaining the orientation information of the capsule endoscope according to the acceleration data and the magnetic field data when the polarization direction is non-horizontal.

Preferably, an external magnet provides the external magnetic field, the method further comprising: obtaining the polarization direction of the external magnet according to position coordinates and tilt angle of the external magnet.

Preferably, when the polarization direction of the external magnetic field is horizontal, the step of obtaining orientation information of the capsule endoscope comprises: obtaining the horizontal orientation of the capsule endoscope according to the orientation of the horizontal polarization component of the external magnet; obtaining the tilt angle of the capsule endoscope to ground according to the acceleration data.

Preferably, when the polarization direction of the external magnetic field is non-horizontal, the step of obtaining orientation information of the capsule endoscope comprises: obtaining the tilt angle of the capsule endoscope to ground according to the acceleration data; obtaining the distance between the external magnet and the capsule endoscope and the vector angle between the direction vector of the external magnet and the direction vector of the capsule endoscope according to the magnetic field data; obtaining the magnetic field direction of the external magnet in a geodetic coordinate system according to the distance; obtaining the orientation information of the capsule endoscope according to the tilt angle of the capsule endoscope to ground, the vector angle and the magnetic field direction.

Preferably, when the gravity line of the capsule endoscope coincides with the gravity line of the external magnet, a first formula is used to calculate the magnetic field direction of the external magnet in the geodetic coordinate system; and when the gravity line of the capsule endoscope does not coincide with the gravity line of the external magnet, a second formula is used to calculate the magnetic field direction of the external magnet in the geodetic coordinate system.

Preferably, obtaining the distance and the vector angle comprises: obtaining a first sub-magnetic field data representing the internal magnetic field; obtaining a second sub-magnetic field data representing the internal magnetic field and the external magnetic field; obtaining a third sub-magnetic field data representing the external magnetic field according to the first sub-magnetic field data and the second sub-magnetic field data; obtaining the distance between the external magnet and the capsule endoscope according to the third sub-magnetic field data; and obtaining the vector angle between the direction vector of the external magnet and the direction vector of the capsule endoscope according to the second sub-magnetic field data and the third sub-magnetic field data.

Preferably, obtaining the magnetic field data according to the external magnetic field and the internal magnetic field comprises: obtaining a magnetic field value according to the internal magnetic field and the external magnetic field; obtaining the magnetic field data according to the magnetic field value. Obtaining the acceleration data of the capsule endoscope comprises: obtaining an acceleration value of the capsule endoscope; and obtaining the acceleration data according to the acceleration value.

Preferably, the method further comprises: detecting the position coordinates of the capsule endoscope to obtain position information of the capsule endoscope. When the polarization direction of the external magnetic field is horizontal, the horizontal position coordinates of the capsule endoscope are the same as those of the external magnet. When the polarization direction of the external magnetic field is non-horizontal and the gravity line of the capsule endoscope coincides with the gravity line of the external magnet, the horizontal position coordinates of the capsule endoscope are obtained according to the horizontal position of the external magnet and the magnetic field data. When the polarization direction of the external magnetic field is non-horizontal, and the gravity line of the capsule endoscope does not coincide with the gravity line of the external magnet, a three-dimensional energized coil obtains the position coordinates of the capsule endoscope.

According to another aspect of the present invention, a capsule endoscope system is provided. The system comprises: an external magnet that provides an external magnetic field; a capsule endoscope that comprises an internal magnetic field and provides acceleration data, wherein the magnetic field data is obtained according to the external magnetic field and the internal magnetic field; and a data processing device that obtains the orientation information of the capsule endoscope according to the acceleration data and the magnetic field data. When the polarization direction of the external magnetic field is horizontal, the data processing device obtains the orientation information of the capsule endoscope according to the acceleration data. When the polarization direction of the external magnetic field is non-horizontal, the data processing device obtains the orientation information of the capsule endoscope according to the acceleration data and the magnetic field data.

Preferably, the capsule endoscope comprises: an internal magnet that provides an internal magnetic field; an acceleration sensor that obtains an acceleration value of the capsule endoscope; a magnetic field sensor that obtains a magnetic field value according to the internal magnetic field and the external magnetic field; and a microprocessor that obtains the acceleration data according to the acceleration value, and obtain the magnetic field data according to the magnetic field value.

Preferably, the polarization direction of the internal magnet is along the direction of the long axis of the capsule endoscope.

Preferably, the data measurement axis of the acceleration sensor, the data measurement axis of the magnetic field sensor, and the central axis of the internal magnet coincide with the central axis of the capsule endoscope.

Preferably, the capsule endoscope further comprises an antenna module for radiating radio frequency signals representing the acceleration data and the magnetic field data.

Preferably, the method further comprises a three-dimensional energized coil that detects the position coordinates of the capsule endoscope.

According to aspects of the present invention, the method and system for determining orientation of a capsule endoscope can accurately obtain the orientation information of the capsule endoscope when the external magnetic field is in any state, and reduce the requirement for the external magnetic field while achieving an accurate orientation of the capsule endoscope, which is convenient for a operator.

Furthermore, the method for determining orientation of a capsule endoscope has a simple calculation process which facilitates the real-time detection of orientation information. Furthermore, in the capsule endoscope system, the capsule endoscope is simple in structure and easy to implement.

BRIEF DESCRIPTION OF THE DRAWINGS

The above and other objects and advantages of the invention can be apparent upon consideration of the following detailed description, taken in conjunction with the accompanying drawings, in which the reference characters refer to like parts throughout and in which.

Figure 1:
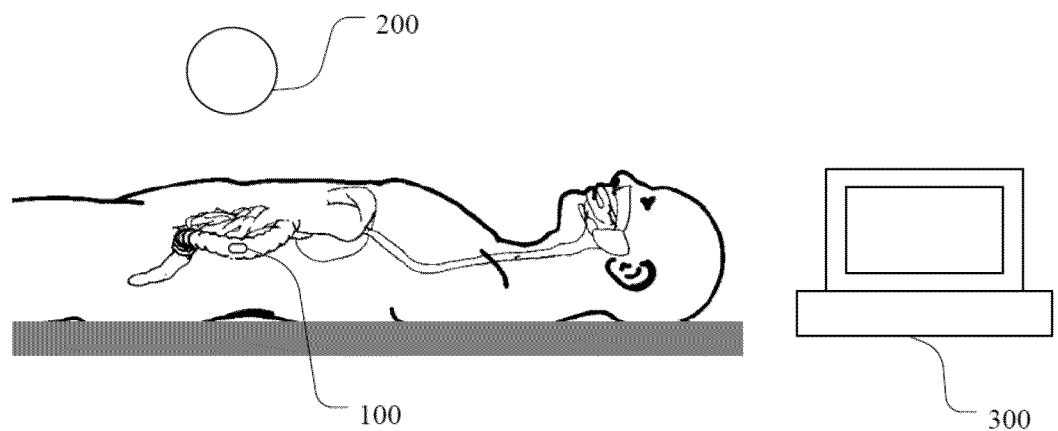
FIG. 1 is a schematic view of a capsule endoscope system, in accordance with some embodiments of the present invention.

Elements in the drawings are: 10. Capsule endoscope system; 100. Capsule endoscope; 101. Enclosure; 110. Power source; 120. Camera module; 130. Microprocessor; 140. Internal magnet; 150. Acceleration sensor; 160. Magnetic field sensor; 170. Antenna module; 200. External magnet; 300. Data processing device.

DETAILED DESCRIPTION

The present invention can be described in more detail below with reference to the accompanying drawings. In the drawings, the same elements are represented by similar markings. For simplicity and clarity of illustration, elements shown in the drawings have not been drawn to scale. the various parts of the drawing are not drawn to scale. In addition, some well-known parts may not be shown in the drawings.

In the present invention, the term "capsule endoscope" refers to an endoscope that can enter body lumen without a tube and should not be construed as a limitation on its shape, dimensions or size. It communicates with an external device by means of wireless communication, thus avoiding the need for a traditional endoscope that transfers light or information through a tube, thereby avoiding pain and trauma to human body.

The term "horizontal orientation" refers to the direction indicated by the long axis of the capsule endoscope when the polarization direction of an external magnet is horizontal and the capsule endoscope is horizontal.

In addition, unless otherwise specified, "internal" refers to the inside of the capsule endoscope, and "external" refers to the outside of the capsule endoscope.

It should be appreciated that A and B being connected/coupled as described in the embodiments of the present invention indicates that A and B may be connected in series or in parallel, or that A and B are connected in series or in parallel by other devices, which are not limited in the embodiments.

Specific embodiments of the present invention are described in further detail below in conjunction with the accompanying drawings.

FIG. 1 is a schematic view of a capsule endoscope system, in accordance with some embodiments of the present invention.

As shown in FIG. 1, the capsule endoscope system 10 comprises a capsule endoscope 100, an external magnet 200 and a data processing device 300.

The capsule endoscope 100 is located in a subject. For example, the subject swallows the capsule endoscope 100 into the digestive tract of the subject. The capsule endoscope 100 moves with peristalsis of the digestive tract and takes images of various regions of the digestive tract. The images can be transmitted to the data processing device 300 in real time, or stored in the capsule endoscope 100.

In the embodiments of the present invention, the orientation of the external magnet 200 may be in any direction. Preferably, the external magnet 200 is a spherical magnet, and the magnetic field of the spherical magnet is simple, which is conducive to reducing the amount of calculation and accelerating the rate of calculation of orientation information of the capsule endoscope 100.

The capsule endoscope 100 is integrated with an acceleration sensor, a magnetic field sensor and a microprocessor, and comprises an internal magnet. The acceleration sensor can obtain acceleration values and the magnetic field sensor can obtain magnetic field values. The microprocessor is used for converting the acceleration values into acceleration data and converting the magnetic field values into magnetic field data.

The data processing device 300 at least comprises a data receiver, which receives acceleration data, magnetic field data and other parameters and analyze them to obtain orientation information of the capsule endoscope 100. More specifically, the data receiver obtains the orientation information of the capsule endoscope 100 according to the position coordinates, acceleration data and magnetic field data of the capsule endoscope 100, as well as the orientation and magnetic field data of the external magnet 200.

In the embodiment, since the external magnet 200 is located outside the subject, its coordinates and tilt angle are easy to obtain (for example, the state of the external magnet 200 is obtained in real time using magnetic ball control software). Taking its coordinates and tilt angle as known parameters can obtain the orientation of the external magnet 200. When the magnetic field polarization direction of the external magnet is horizontal or non-horizontal, different methods are used to calculate the orientation information of the capsule endoscope 100 respectively. Further, the position coordinates of the capsule endoscope 100 can be obtained in a variety of ways. For example, when the capsule endoscope 100 is not located directly below the external magnet 200, a three-dimensional energized coil is used to calculate three distances between the capsule endoscope 100 and the coil, and the three distances are used to determine the position coordinates of the capsule endoscope 100. It should be appreciated that the present invention does not limit the way of obtaining the position coordinates of the capsule endoscope 100 and the orientation of the external magnet 200.

In an alternative embodiment, the data processing device 300 adjusts the orientation of the capsule endoscope 100 based on the orientation information, so as to acquire images of the digestive tract in multiple directions. In the embodiment, for example, the capsule endoscope system 10 further comprises a magnetic control device that can receive control signals from the data processing device 300, and apply a force to the internal magnet of the capsule endoscope 100 to change the orientation of the capsule endoscope 100.

The principle of the capsule endoscope system provided in the present invention can be described in detail below.

Figure 2:
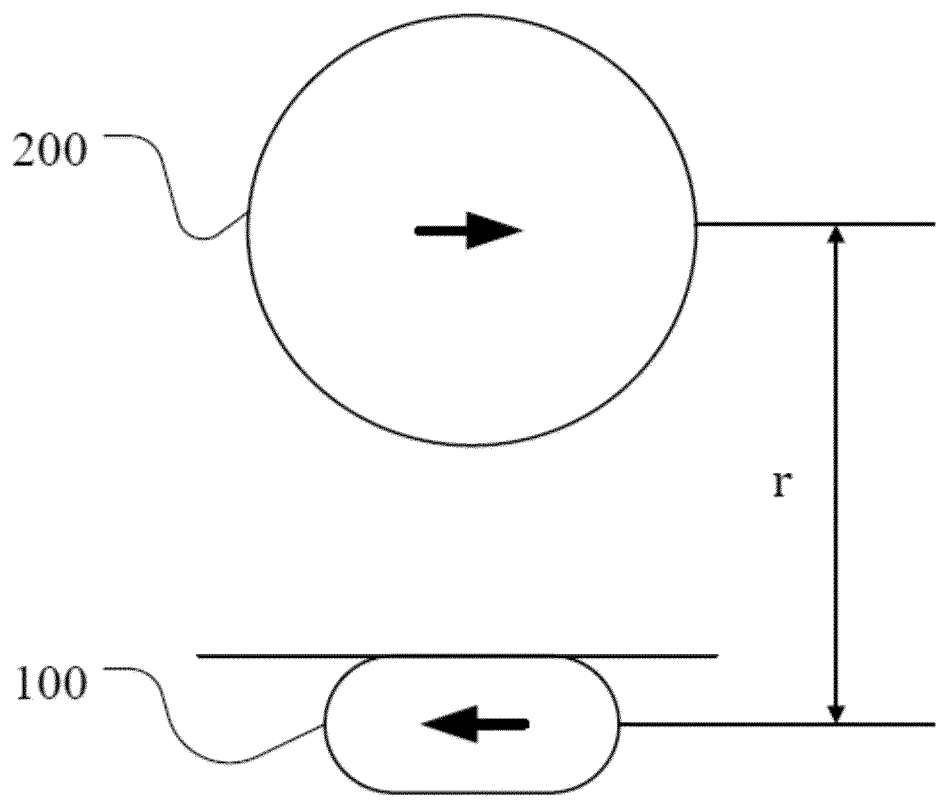
FIG. 2 illustrates the direction of magnetization of a capsule endoscope system, in accordance with a first embodiment of the present invention.

FIG. 2 illustrates the direction of magnetization of a capsule endoscope system, in accordance with a first embodiment of the present invention.

As shown in FIG. 2, when the external magnet 200 is in a horizontal direction, it can be considered that the capsule endoscope 100 is also in a horizontal direction. In an actual working process of the capsule endoscope system, the foregoing logic holds true since the stomach inside is a cavity when it is in a filled state.

The internal magnet of the capsule endoscope 100 is disposed along the long axis of the capsule endoscope 100 to become an approximately axisymmetric magnet, and the NS direction of the capsule endoscope 100 is opposite to the NS direction of the external magnet 200, the NS direction sees the direction indicated by an arrow in FIG. 2. An acceleration sensor and a microprocessor are integrated inside the capsule endoscope 100. The z-axis (data measurement axis) of the acceleration sensor is parallel to the long axis of the capsule endoscope 100 to obtain the acceleration values. The microprocessor acquires the acceleration data based on this acceleration values and transmits the acceleration data through an antenna module of the capsule endoscope 100 to the external data processing device for calculation.

In the embodiment, the planar coordinate position (x, y) of the capsule endoscope 100 is consistent with the planar coordinate position (x, y) of the external magnet 200, and the horizontal orientation of the capsule endoscope 100 is the orientation of horizontal polarization component of the external magnet 200. The tilt angle of the capsule endoscope 100 to ground is calculated using the acceleration data. The formula (1) for calculating the tilt angle is as follows:

$$\cos\varphi = \frac{g_z}{g}, \tag{1}$$

where, $\varphi$ is the tilt angle of the capsule endoscope 100 to ground, $g_z$ is the z-axis component of the acceleration data of the capsule endoscope 100, g is the gravitational acceleration. In the embodiment of the present invention, the gravitational acceleration g is the total acceleration measured by the acceleration sensor, $g=\sqrt{g_x^2+g_y^2+g_z^2}$, of which the value does not differ much from 9.8. In some alternative embodiments, it can be considered that the gravitational acceleration in the environment where the capsule endoscope 100 is located is a known parameter, so a gravity sensor is used instead of the acceleration sensor to reduce costs and to reduce the number of calculations.

Thus, while the external magnetic field provided by the external magnet 200 is in a horizontal direction, the capsule endoscope 100 can sense its orientation information with an acceleration sensor. Specifically, the orientation information comprises the horizontal orientation and the tilt angle of the capsule endoscope to ground, and the position information comprises its planar coordinate position.

Figure 3:
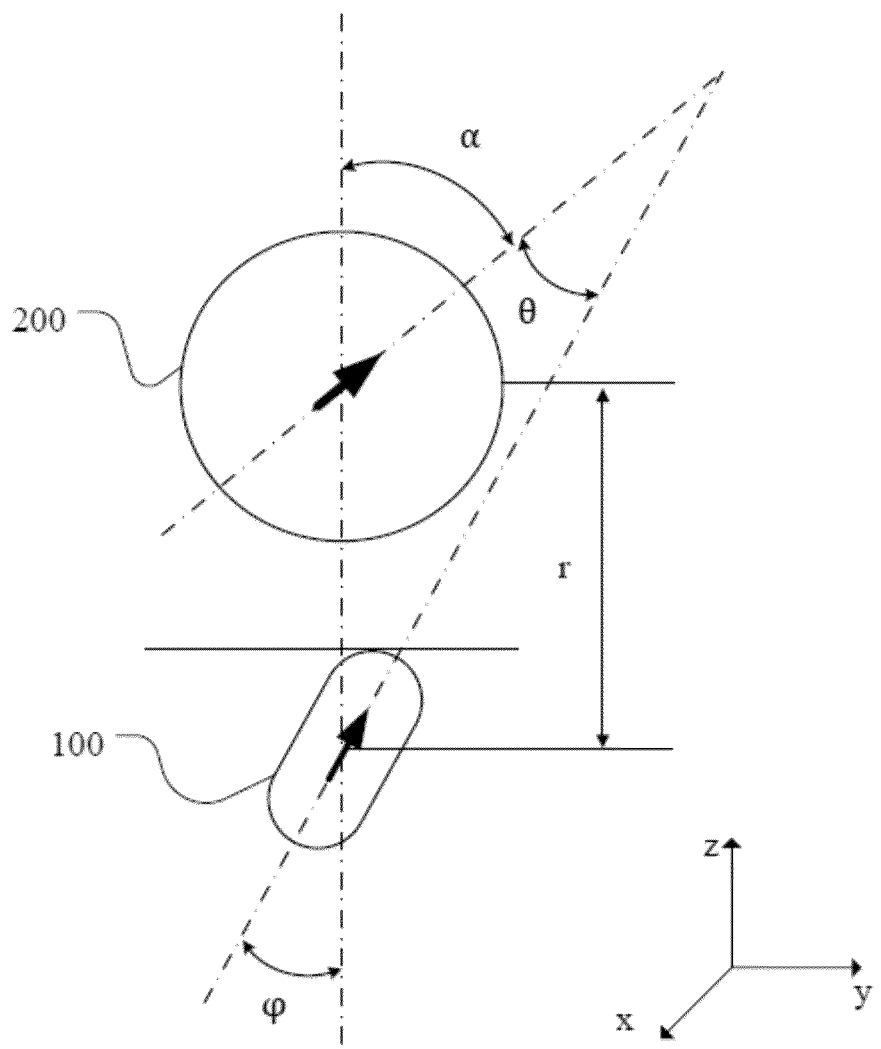
FIG. 3 illustrates the direction of magnetization of a capsule endoscope system, in accordance with a second embodiment of the present invention.

FIG. 3 illustrates the direction of magnetization of a capsule endoscope system, in accordance with a second embodiment of the present invention. In FIG. 3, for clarity of illustration, only a schematic view of the capsule endoscope system in an yz plane is shown, with the x-axis indicating a direction perpendicular to the yz plane.

As shown in FIG. 3, the external magnet 200 is in a non-horizontal direction, the tilt angle of the external magnet 200 is α, and the vector angle between the direction vector of the capsule endoscope 100 and the direction vector of the external magnet 200 is θ. The internal magnet of the capsule endoscope 100 is disposed along the long axis of the capsule endoscope 100 to become an approximately axisymmetric magnet. An acceleration sensor and a magnetic field sensor are integrated inside the capsule endoscope 100. The z-axis of the acceleration sensor is parallel to the long axis of the capsule endoscope to obtain the acceleration values. The z-axis of the magnetic field sensor is parallel to the long axis of the capsule endoscope to obtain the magnetic field values. The microprocessor acquires the acceleration data and the magnetic field data based on the acceleration values and the magnetic field values, and transmits them through the antenna module to the external data processing device for calculation.

In the embodiment, the external magnet 200 attracts the capsule endoscope 100 so that the capsule endoscope 100 is directly below the external magnet 200. The tilt angle of the capsule endoscope 100 to ground is calculated using the acceleration data. The formula for calculating the tilt angle is the same as the formula (1) in FIG. 2, and the formula (1) is as follows:

$$\cos\varphi = \frac{g_z}{g}, \tag{1}$$

where, φ is the tilt angle of the capsule endoscope 100 to ground, $g_z$ is the z-axis component of the acceleration data of the capsule endoscope, g is the gravitational acceleration.

When the polarization direction of the external magnet 200 is vertical, the magnetic field sensor reads the magnetic field value $B_t = B + B_e$, where, $B_t$ is a measured value of the magnetic field sensor, B is a magnetic field generated by the external magnet 200 at the position of the magnetic field sensor, and $B_e$ is a magnetic field generated by the internal magnet of the capsule endoscope 100. In the embodiment, after the capsule endoscope 100 is turned on and placed in an environment away from magnetic environment, the magnetic field sensor reading is $B_e$. Therefore, $B_e$ can be used as a known parameter in the capsule endoscope 100.

The external magnet 200 attracts the capsule endoscope 100 to directly below the external magnet 200. The value of B is obtained according to the reading of the magnetic field sensor. The distance r between the center of the external magnet 200 and the magnetic field sensor of the capsule endoscope 100 is calculated. The formula (2) for calculating the distance r is as follows:

$$B = \frac{\mu_0}{4\pi} \times \frac{2M}{r^3}, \tag{2}$$

where, $\mu_0$ is the permeability of the magnetic field in a vacuum, and M is the magnetic moment.

Assuming that the spherical center coordinates of the external magnet 200 are (x, y, z), the position coordinates of the capsule endoscope 100 are (x, y, z-r).

At this point, the angle between the polarization direction of the external magnet 200 and the x-axis is β, then the magnetic field value can be expressed by formulas (3a), (3b) and (3c) as:

$$B_x = \frac{\mu_0}{4\pi} \times \frac{2M\sin\alpha\cos\beta}{r^3} \tag{3a}$$

$$B_y = -\frac{\mu_0}{4\pi} \times \frac{2M\sin\alpha\sin\beta}{r^3} \tag{3b}$$

$$B_z = \frac{\mu_0}{4\pi} \times \frac{2M\cos\alpha}{r^3}. \tag{3c}$$

In the embodiment, the magnetic field direction of the external magnet 200 is defined as $$(\hat{n}_x, \hat{n}_y, \hat{n}_z) = \frac{1}{\sqrt{1+3\cos\alpha^2}}(\sin\alpha\cos\beta, -\sin\alpha\sin\beta, \cos\alpha) = (a, b, c). \tag{3d}$$

The formulas (3a)-(3d) here are referred to as the first formula hereinafter.

In the geodesic coordinate system: $\vec{B}=(a, b, c)$, $\vec{g}=(0,0,1)$, the direction of the capsule endoscope 100 is $\vec{N}=(\hat{x}, \hat{y}, \hat{z})$, the vector angle between the direction vector of the capsule endoscope 100 and the direction vector of the external magnet 200 is θ, and the formula (4) for calculating the vector angle θ is:

$$\cos\theta = \frac{B_{z'}}{B}, \tag{4}$$

where, $B_{z'}$ is the z-axis reading on the magnetic field sensor. Further, based on the angle φ between the capsule endoscope 100 and gravity, the orientation information is calculated. The calculation formula and solving process are as follows:

$$\vec{N} \cdot \vec{B} = NB \cos\theta \tag{5a}$$

$$\vec{N} \cdot \vec{g} = Ng \cos\varphi \tag{5b}$$

$$(\hat{x}, \hat{y}, \hat{z}) \cdot (a, b, c) = ax + by + cz = \cos\theta \tag{5c}$$

$$(\hat{x}, \hat{y}, \hat{z}) \cdot (0, 0, 1) = z = \cos\varphi \tag{5d}.$$

Moreover, $$x^2 + y^2 + z^2 = 1 \tag{5e}.$$

Then, according to the formulas (5a)~(5e), $$x^2 + y^2 = 1 - \cos\varphi^2 \tag{6}$$

$$x = \frac{1}{a}(\cos\theta - c \cdot \cos\varphi - by) \tag{7a}$$

$$y = \frac{b(\cos\theta - c \cdot \cos\varphi) \pm \sqrt{a^2(a^2+b^2)(1-\cos\varphi^2) - a^2(\cos\theta - c \cdot \cos\varphi)^2}}{a^2+b^2} \tag{7b}$$

$$z = \cos\varphi. \tag{7c}$$

From the above derivation process, it can be seen that the orientation information of the capsule endoscope 100 can be obtained by acquiring the acceleration data $g_z$, the gravitational acceleration g, the magnetic field data B and $B_{z'}$, the vector angle θ between the direction vector of the capsule endoscope 100 and the direction vector of the external magnet 200, and the angle β between the polarization direction of the external magnet 200 and the x-axis. The orientation information is the vector (x, y, z) representing the magnetic field orientation of the capsule endoscope 100, as shown in formulas (7a) to (7c). Since the external magnet 200 is outside the human body, a plurality of existing methods are available to measure the vector angle θ between the direction vector of the capsule endoscope 100 and the direction vector of the external magnet 200 and the angle β between the polarization direction of the external magnet 200 and the x-axis.

Further, the planar coordinate position of the capsule endoscope 100 is consistent with that of the external magnet 200, so the position information of the capsule endoscope 100 can be determined based on the plane position coordinates of the external magnet 200.

Figure 4:
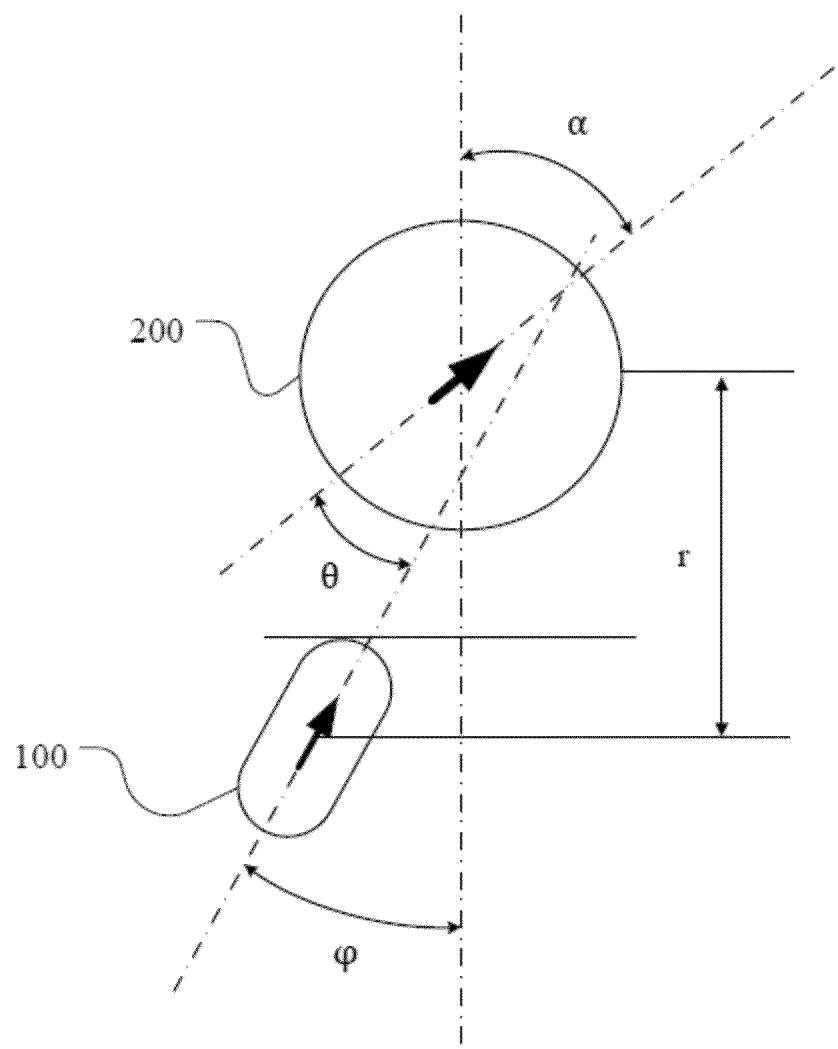
FIG. 4 illustrates the direction of magnetization of a capsule endoscope system, in accordance with a third embodiment of the present invention.

FIG. 4 illustrates the direction of magnetization of a capsule endoscope system, in accordance with a third embodiment of the present invention. In FIG. 4, for clarity of illustration, only a schematic view of the capsule endoscope system in an yz plane is shown, with the x-axis indicating a direction perpendicular to the yz plane.

As shown in FIG. 4, the external magnet 200 is in a non-horizontal direction, the tilt angle of the external magnet 200 is a, and the vector angle between the direction vector of the capsule endoscope 100 and the direction vector of the external magnet 200 is θ. The internal magnet of the capsule endoscope 100 is disposed along the long axis of the capsule endoscope 100 to become an approximately axisymmetric magnet. An acceleration sensor and a magnetic field sensor are integrated inside the capsule endoscope 100. The z-axis of the acceleration sensor is parallel to the long axis of the capsule to obtain the acceleration values. The z-axis of the magnetic field sensor is parallel to the long axis of the capsule to obtain the magnetic field values. The microprocessor acquires the acceleration data and the magnetic field data based on the acceleration values and the magnetic field values, and transmits them through the antenna module to the external data processing device for calculation.

The derivation process of orientation information of the capsule endoscope in the capsule endoscope system as shown in FIG. 4 is approximately the same as that shown in FIG. 3, with the difference being the magnetic field direction $\vec{B}$=(a, b, c) of the external magnet 200 in the geodesic coordinate system, and the similarities is not repeated for clarity.

In the embodiment, the position of the external magnet 200 is defined as $(x_0, y_0, z_0)$, and the polarization direction of the external magnet 200 is defined as $(m_x, m_y, m_z)$=M (sin α cos β, −sin α sin β, cos α).

Further, the direction of the external magnet 200 is expressed as in Formulas (8a) to (8h). The Formulas (8a) to (8h) are hereinafter referred to as a second formula.

$$\vec{B}(\vec{r}) = \frac{\mu_0}{4\pi}\left[\frac{3\vec{r}(\vec{m}\cdot\vec{r}) - \vec{m}}{r^3}\right] \quad (8a)$$

$$r = \sqrt{(x_0 - x)^2 + (y_0 - y)^2 + (z_0 - z)^2} \quad (8b)$$

$$\hat{r} = \left(\frac{x_0-x}{r}\hat{x}, \frac{y_0-y}{r}\hat{y}, \frac{z_0-z}{r}\hat{z}\right) = (\bar{x}\hat{x}, \bar{y}\hat{y}, \bar{z}\hat{z}) \quad (8c)$$

$$\vec{B} = \frac{\mu_0}{4\pi r^3}[3\hat{r}(m_x\bar{x}+m_y\bar{y}+m_z\bar{z}) - m_x\hat{x} - m_y\hat{y} - m_z\hat{z}] = \quad (8d)$$

$$\frac{\mu_0}{4\pi r^3}\{[3(m_x\bar{x}+m_y\bar{y}+m_z\bar{z})\bar{x} - m_x]\hat{x} + [3(m_x\bar{x}+m_y\bar{y}+m_z\bar{z})\bar{y} - m_y]\hat{y}$$

$$+ [3(m_x\bar{x}+m_y\bar{y}+m_z\bar{z})\bar{z} - m_z]\hat{z}\}$$

-continued $$B_x = \frac{\mu_0}{4\pi r^3}[3(m_x\bar{x}+m_y\bar{y}+m_z\bar{z})\bar{x} - m_x]\hat{x} \quad (8e)$$

$$B_y = \frac{\mu_0}{4\pi r^3}[3(m_x\bar{x}+m_y\bar{y}+m_z\bar{z})\bar{x} - m_y]\hat{y} \quad (8f)$$

$$B_z = \frac{\mu_0}{4\pi r^3}[3(m_x\bar{x}+m_y\bar{y}+m_z\bar{z})\bar{x} - m_z]\hat{z} \quad (8g)$$

$$\vec{B} \rightarrow (a, b, c) = \left(\frac{B_x}{\sqrt{B_x^2+B_y^2+B_z^2}}, \frac{B_y}{\sqrt{B_x^2+B_y^2+B_z^2}}, \frac{B_z}{\sqrt{B_x^2+B_y^2+B_z^2}}\right) \quad (8h)$$

In the geodesic coordinate system: $\vec{B}$=(a, b, c), $\vec{g}$=(0,0,1), the direction of the capsule endoscope 100 is $\vec{N}$=($\hat{x}$, $\hat{y}$, $\hat{z}$), the vector angle between the direction vector of the capsule endoscope 100 and the direction vector of the external magnet 200 is θ, the angle between the capsule endoscope 100 and gravity is φ. In addition, according to the description for FIG. 3, the orientation information of the capsule endoscope 100 is obtained as shown in formulas (9a) to (9c):

$$x = \frac{1}{a}(\cos\theta - c\cdot\cos\phi - by) \quad (9a)$$

$$y = \frac{b(\cos\theta - c\cdot\cos\varphi) \pm \sqrt{a^2(a^2+b^2)(1-\cos\varphi^2) - a^2(\cos\theta - c\cdot\cos\varphi)^2}}{a^2+b^2} \quad (9b)$$

$$z = \cos\varphi. \quad (9c)$$

From the above derivation process, it can be seen that the orientation information of the capsule endoscope 100 can be obtained by acquiring the acceleration data $g_z$, the gravitational acceleration g, the magnetic field data B and $B_{z'}$, the vector angle θ between the direction vector of the capsule endoscope 100 and the direction vector of the external magnet 200, and the angle β between the polarization direction of the external magnet 200 and the x-axis. The orientation information is the vector (x, y, z) representing the magnetic field orientation of the capsule endoscope 100, as shown in formulas (9a) to (9c). Since the external magnet 200 is outside the human body, a plurality of existing methods are available to measure the vector angle θ between the direction vector of the capsule endoscope 100 and the direction vector of the external magnet 200 and the angle β between the polarization direction of the external magnet 200 and the x-axis.

In the embodiment, the capsule endoscope 100 is located at any position of the external magnet. Optionally, in order to obtain the spatial position of the capsule endoscope 100, three three-dimensional energized coils (not shown) are placed in the external space of the capsule endoscope 100. Based on the magnetic field value sensed by the magnetic field sensor of the capsule endoscope 100, the distances between the capsule endoscope 100 and the three coils are obtained, thereby determining the spatial position (x, y, z) of the capsule endoscope 100 to obtain the position information of the capsule endoscope 100.

Figure 5:
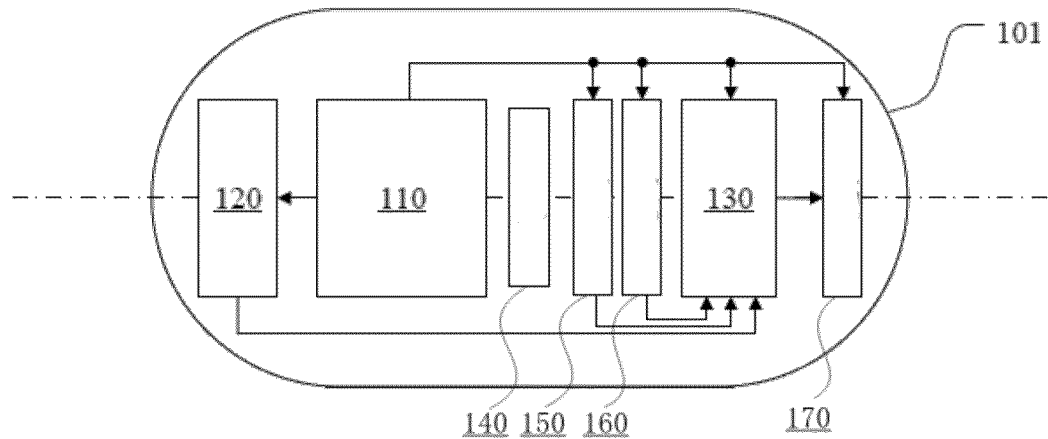
FIG. 5 is a schematic view of a capsule endoscope, in accordance with some embodiments of the present invention.

FIG. 5 is a schematic view of a capsule endoscope, in accordance with some embodiments of the present invention.

As shown in FIG. 5, the capsule endoscope 100 comprises a power source 110, a camera module 120, a microprocessor 130, an internal magnet 140, an acceleration sensor 150, a magnetic field sensor 160, and an antenna module 170.

Electronic components are all sealed in an enclosure 101 to avoid being corroded by body fluids.

It should be appreciated and understood that FIG. 5 shows a schematic view of the components inside the capsule endoscope 100, which is solely to illustrate the signaling relationships between the elements and should not be construed as a limitation on their shape, size, or location.

The power source 110 is used to supply voltage and/or current required by other components in the capsule endoscope 100. In the embodiment of the present invention, the power source 110 supplies operating voltage to the camera module 120, the microprocessor 130, the acceleration sensor 150, the magnetic field sensor 160 and the antenna module 170. In some examples, the power source 110 has a plurality of output terminals, each of which provides different currents or voltages to meet the power supply requirements of the components.

The camera module 120 is used to take images and generate image data corresponding to the images. The camera module 120 comprises, for example, an illuminating source and an imaging element. A portion of the enclosure 101 corresponding to the camera module 120 is made transparent, so that the camera module 120 can take images through the enclosure 101.

The microprocessor 130 receives the image data from the camera module 120, and converts the image data into a modulated signal. The antenna module 170 comprises, for example, a radio frequency module and a transmitting antenna. The antenna module 170 receives the modulated signal and radiates it to an external data processing device. For example, the radio frequency module converts the modulated signal into a radio frequency signal, and the transmitting antenna radiates the radio frequency signal, thereby completing transmission of the modulated signal to the external data processing device. In a preferred embodiment, the antenna module 170 comprises an antenna transceiver module and a transceiver antenna, thereby providing a signal transceiver function.

In the design of a traditional capsule endoscope, a magnetic field sensor is typically used to determine the orientation of the capsule endoscope and transmit the obtained data to a data processor to obtain the orientation information of the capsule endoscope. Specifically, a magnetic field sensor is integrated inside the capsule endoscope, and an external magnetic field is provided at a location corresponding to the capsule endoscope outside the body of the subject. During determining the orientation of the capsule endoscope, the direction of the external magnetic field needs to be kept horizontal. However, because of the need to change the orientation of the capsule endoscope during an examination, it is difficult to keep the external magnetic field horizontal, which in turn leads to a large error in the orientation information. The present invention provides a capsule endoscope system, to accurately detect the orientation information of a capsule endoscope even when its external magnetic field is in a non-horizontal direction.

The capsule endoscope 100 in accordance with the embodiments of the present invention is provided with an internal magnet 140, an acceleration sensor 150, and a magnetic field sensor 160 to determine the orientation of the capsule endoscope 100.

In the embodiments of the present invention, the internal magnet 140 is disposed along the long axis of the capsule endoscope 100 and becomes an approximately axisymmetric magnet whose polarization direction is also along the long axis of the capsule endoscope 100, the long axis is shown as a dashed line in FIG. 5. Optionally, the internal magnet 140 is a cylindrical magnet or a spherical magnet.

The acceleration sensor 150 is used to detect the acceleration values of the capsule endoscope 100 and transmit the acceleration values to the microprocessor 130. The microprocessor 130 obtains the acceleration data of the capsule endoscope 100 according to the acceleration values.

As an example, the acceleration sensor 150 works according to the principle of piezoelectric effect. The piezoelectric effect refers to that "For a heteropolar crystal without a center of symmetry, an external force applied thereto, in addition to deforming the crystal, can change the polarization state of the crystal and create an electric field inside the crystal, and this phenomenon of polarization of a medium due to a mechanical force is called positive piezoelectric effect". In the example, the acceleration sensor 150 makes use of the internal crystal deformation characteristic due to acceleration. Since the crystal deformation generates a voltage, it can output a voltage representing the acceleration value by calculating the relationship between the voltage and the acceleration value.

It should be appreciated that, in accordance with embodiments of the present invention, the acceleration sensor 150 may also be made using other principles. The principles described herein are, for example, but not limited to, the principles of capacitance effect, thermal bubble effect, light effect, etc., which can produce deformation in response to changes in acceleration.

The magnetic field sensor 160 is used to obtain magnetic field values and transmit the magnetic field values to the microprocessor 130. The magnetic field values represent the magnetic field data of the internal magnet 140 and the external magnet. The microprocessor 130 obtains the magnetic field data of the internal magnet 140 and the magnetic field data of the external magnet according to the magnetic field values.

In the embodiments of the present invention, the data processing device 300 placed outside the subject receives the acceleration data and the magnetic field data from the microprocessor 130. Then, according to the acceleration data, the data processing device 300 obtains the tilt angle of the capsule endoscope 100 to ground from the acceleration sensor 150 and the magnetic field sensor 160. According to the magnetic field data, the data processing device 300 obtains the vector angle between the direction vector of the capsule endoscope 100 and the direction vector of the external magnet 200. Based on at least the tilt angle and the angle between the direction vector of the capsule endoscope 100 and the direction vector of the external magnet 200, the data processing device obtains the orientation information of the capsule endoscope 100. The specific calculation principle of the data processing device 300 can be found in the description above for FIGS. 2-4. The calculation process can be implemented, for example, by software programming or a combination of software and hardware.

The foregoing describes some examples of the capsule endoscope 100 in accordance some embodiments of the present invention. However, the embodiments of the present invention are not limited thereto, and there may be other expansions and deformations.

It may be realized by persons skilled in the art that, in conjunction with the structure and method of each example described in the embodiments disclosed herein, the described functions may be achieved using different methods of configuration or adjustment for each structure or reasonable variations of that structure, but such implementations should not be considered beyond the scope of the present invention. Also, it should be understood that the foregoing description of the connection relationship between various components of the capsule endoscope in the embodiments of the present invention is intended to be illustrative and is not construed as limiting the embodiments of the present invention.

Figure 6:
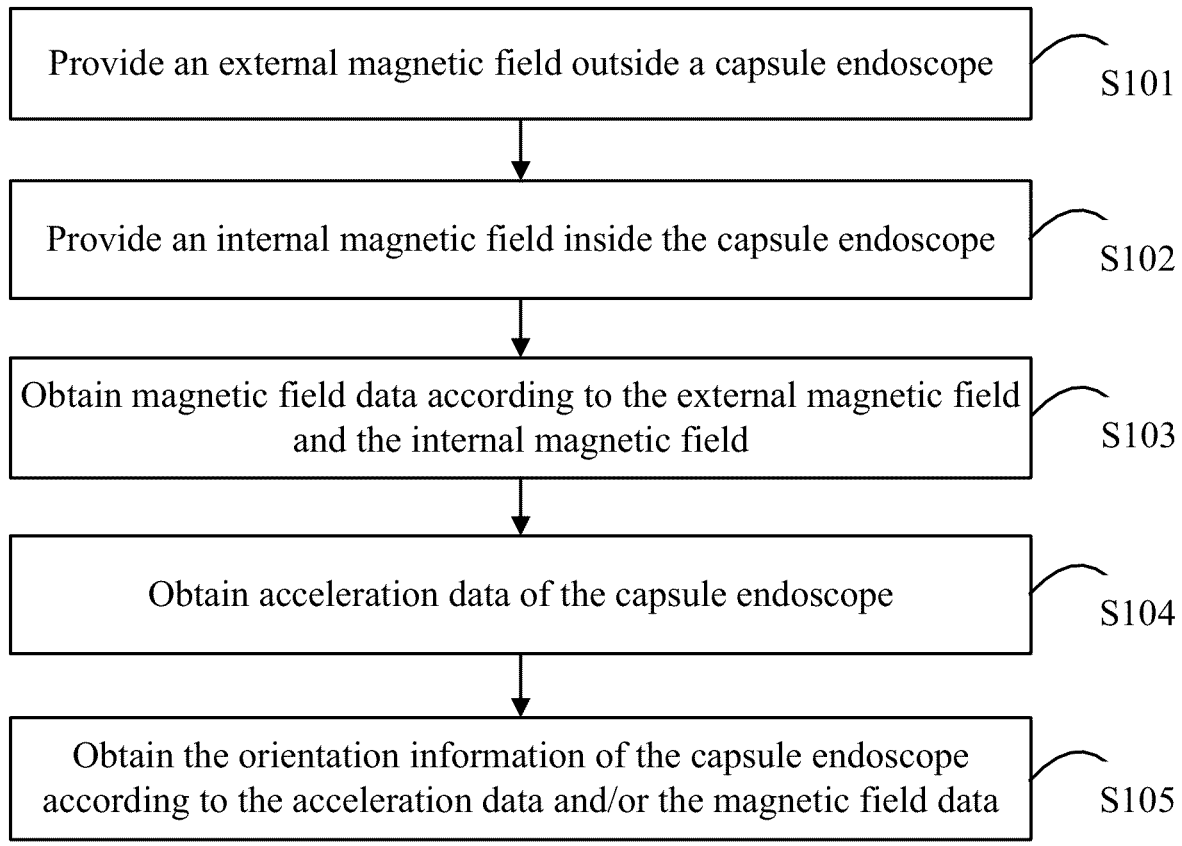
FIG. 6 is a schematic flowchart of a method for determining orientation of a capsule endoscope, in accordance with some embodiments of the present invention.

FIG. 6 is a schematic flowchart of a method for determining orientation of a capsule endoscope, in accordance with some embodiments of the present invention.

Step S101, providing an external magnetic field outside the capsule endoscope. An external magnet is used to provide the external magnetic field, the polarization direction of the external magnet is obtained according to the position coordinates and tilt angle of the external magnet.

Step S102, providing an internal magnetic field inside the capsule endoscope. In an embodiment of the present invention, the polarization direction of the external magnetic field is horizontal or non-horizontal.

Step S103, obtaining magnetic field data according to the external magnetic field and the internal magnetic field. Specifically, the step for obtaining magnetic field data according to the external magnetic field and the internal magnetic field comprises: obtaining magnetic field values according to the internal magnetic field and the external magnetic field; obtaining magnetic field data according to the magnetic field values.

Step S104, obtaining acceleration data of the capsule endoscope. Specifically, the step for obtaining the acceleration data of the capsule endoscope comprises: obtaining acceleration values of the capsule endoscope; and obtaining the acceleration data according to the acceleration values.

Step S105, obtaining the orientation information of the capsule endoscope according to the acceleration data and/or the magnetic field data. In the embodiments of the present invention, when the polarization direction of the external magnetic field is horizontal or non-horizontal relative to the polarization direction of the internal magnetic field, different methods are used to calculate the orientation information of the capsule endoscope. For the specific derivation principle, please refer to the above description with respect to FIGS. 2-4.

Obtaining orientation information of the capsule endoscope when the polarization direction of the external magnetic field is horizontal comprises: obtaining the horizontal orientation of the capsule endoscope according to the orientation of the horizontal polarization component of the external magnet; obtaining the tilt angle of the capsule endoscope to ground according to the acceleration data.

Obtaining orientation information of the capsule endoscope when the polarization direction of the external magnetic field is non-horizontal comprises: obtaining the tilt angle of the capsule endoscope to ground according to the acceleration data; obtaining the distance between the external magnet and the capsule endoscope and the vector angle between the direction vector of the external magnet and the direction vector of the capsule endoscope according to the magnetic field data; obtaining the magnetic field direction of the external magnet in a geodetic coordinate system according to the distance; obtaining the orientation information of the capsule endoscope according to the tilt angle of the capsule endoscope to ground, the vector angle between the direction vector of the external magnet and the direction vector of the capsule endoscope and the magnetic field direction.

When the gravity line of the capsule endoscope coincides with the gravity line of the external magnet, a first formula is used to calculate the magnetic field direction of the external magnet in the geodetic coordinate system. For the first formula, please refer to the description of FIG. 3 above. When the gravity line of the capsule endoscope does not coincide with the gravity line of the external magnet, a second formula is used to calculate the magnetic field direction of the external magnet in the geodetic coordinate system. For the second formula, please refer to the description of FIG. 4 above Obtaining the distance between the external magnet and the capsule endoscope and the vector angle between the direction vector of the external magnet and the direction vector of the capsule endoscope comprises: obtaining a first sub-magnetic field data representing the internal magnetic field; obtaining a second sub-magnetic field data representing the internal magnetic field and the external magnetic field; obtaining a third sub-magnetic field data representing the external magnetic field according to the first sub-magnetic field data and the second sub-magnetic field data; obtaining the distance between the external magnet and the capsule endoscope according to the third sub-magnetic field data; and obtaining the vector angle between the direction vector of the external magnet and the direction vector of the capsule endoscope according to the second sub-magnetic field data and the third sub-magnetic field data.

Preferably, before performing the step S101 or after performing the step S105, further comprises: detecting the position coordinates of the capsule endoscope to obtain position information of the capsule endoscope, wherein when the polarization direction of the external magnetic field is horizontal, the horizontal position coordinates of the capsule endoscope are the same as those of the external magnet; when the polarization direction of the external magnetic field is non-horizontal, for example a three-dimensional energized coil is used to obtain the position coordinates of the capsule endoscope. When the polarization direction of the external magnetic field is non-horizontal, optionally when the gravity line of the capsule endoscope coincides with the gravity line of the external magnet, obtaining the horizontal position coordinates of the capsule endoscope according to the horizontal position of the external magnet and the magnetic field data; when the gravity line of the capsule endoscope does not coincide with the gravity line of the external magnet, a three-dimensional energized coil is used to obtain the position coordinates of the capsule endoscope.

It should be noted that, relationship terms as described herein such as first and second are used only to distinguish one entity or operation from another, but do not necessarily require or imply any such actual relationship or sequence between these entities or operations. Moreover, the terms "include", "comprise" or any other variant thereof are intended to cover non-exclusive inclusion, so that a process, method, article or device that includes a series of elements includes not only those elements but also other elements that are not explicitly listed or further includes the elements inherent to such process, method, article or device. Without further limitation, the element limited by the statement "comprises a . . . " does not preclude the existence of another identical element in the process, method, article or equipment that includes said element.

In accordance with embodiments of the present invention as described above, these embodiments do not elaborate all details, and do not limit the invention to said embodiments. Obviously, a plurality of modifications and changes can be made based on the above description. These embodiments have been selected and specifically described in this specification in order to better explain the principles and practical applications of the present invention, so those skilled in the art can make good use of the present invention and the modify based on the present invention. The present invention is limited only by the claims and their full scope and equivalents.

What is claimed is:

1. A method for determining orientation of a capsule endoscope, comprising:
providing an external magnetic field outside the capsule endoscope;
providing an internal magnetic field inside the capsule endoscope;
obtaining magnetic field data according to the external magnetic field and the internal magnetic field;
obtaining acceleration data of the capsule endoscope; and
obtaining the orientation information of the capsule endoscope according to the acceleration data when a polarization direction of the external magnetic field is horizontal, and
obtaining the orientation information of the capsule endoscope according to the acceleration data and magnetic field data when the polarization direction is non-horizontal,
wherein when the polarization direction of the external magnetic field is non-horizontal, the step of obtaining orientation information of the capsule endoscope comprises:
obtaining a tilt angle of the capsule endoscope to ground according to the acceleration data;
obtaining a distance between the external magnet and the capsule endoscope and a vector angle between a direction vector of the external magnet and a direction vector of the capsule endoscope according to the magnetic field data;
obtaining a magnetic field direction of the external magnet in a geodetic coordinate system according to the distance;
obtaining the orientation information of the capsule endoscope according to the tilt angle of the capsule endoscope to ground, the vector angle and the magnetic field direction.

2. The method of claim 1, wherein an external magnet provides the external magnetic field, the method further comprising:
obtaining the polarization direction of the external magnet according to position coordinates and tilt angle of the external magnet.

3. The method of claim 2, wherein when the polarization direction of the external magnetic field is horizontal, the step of obtaining orientation information of the capsule endoscope comprises:
obtaining a horizontal orientation of the capsule endoscope based on a direction of a horizontal polarization component of the external magnet; and obtaining a tilt angle of the capsule endoscope relative to a reference ground based on the acceleration data.

4. The method of claim 1, wherein when a gravity line of the capsule endoscope coincides with a gravity line of the external magnet, a first formula is used to calculate the magnetic field direction of the external magnet in the geodetic coordinate system; and wherein when the gravity line of the capsule endoscope does not coincide with the gravity line of the external magnet, a second formula is used to calculate the magnetic field direction of the external magnet in the geodetic coordinate system, the first formula is:

$$(a, b, c) = \frac{1}{\sqrt{1 + 3\cos\alpha^2}}(\sin\alpha\cos\beta, -\sin\alpha\sin\beta, \cos\alpha);$$

the second formula is:

$$(a, b, c) = \frac{1}{\sqrt{1 + 3\cos\alpha^2}}(\sin\alpha\cos\beta, -\sin\alpha\sin\beta, \cos\alpha);$$

wherein (a, b, c) represents the magnetic field direction of the external magnet in the geodetic coordinate system, $\alpha$ is the tilt angle of the external magnet, $\beta$ is an angle between the polarization direction of the external magnet and the x-axis, $B_x$, $B_y$ and $B_z$ respectively represent the x-axis, y-axis, and z-axis components of the magnetic field generated by the external magnet at the position of the magnetic field sensor.

5. The method of claim 1, wherein obtaining the distance and the vector angle comprises:
obtaining a first sub-magnetic field data representing the internal magnetic field;
obtaining a second sub-magnetic field data representing the internal magnetic field and the external magnetic field;
obtaining a third sub-magnetic field data representing the external magnetic field according to the first sub-magnetic field data and the second sub-magnetic field data;
obtaining the distance between the external magnet and the capsule endoscope according to the third sub-magnetic field data; and
obtaining the vector angle between the direction vector of the external magnet and the direction vector of the capsule endoscope according to the second sub-magnetic field data and the third sub-magnetic field data.

6. The method of claim 1, wherein obtaining the magnetic field data according to the external magnetic field and the internal magnetic field comprises:
obtaining a magnetic field value according to the internal magnetic field and the external magnetic field;
obtaining the magnetic field data according to the magnetic field value; and
wherein obtaining the acceleration data of the capsule endoscope comprises:
obtaining an acceleration value of the capsule endoscope; and
obtaining the acceleration data according to the acceleration value.

7. The method of claim 2, further comprising:
detecting the position coordinates of the capsule endoscope to obtain position information of the capsule endoscope, wherein
when the polarization direction of the external magnetic field is horizontal, horizontal position coordinates of the capsule endoscope are the same as those of the external magnet;
when the polarization direction of the external magnetic field is non-horizontal and a gravity line of the capsule endoscope coincides with a gravity line of the external magnet, obtaining the horizontal position coordinates of the capsule endoscope according to the horizontal position of the external magnet and the magnetic field data; and when the polarization direction of the external magnetic field is non-horizontal, and the gravity line of the capsule endoscope does not coincide with the gravity line of the external magnet, a three-dimensional energized coil obtains the position coordinates of the capsule endoscope.

8. A capsule endoscope system, comprising:
an external magnet that provides an external magnetic field;
a capsule endoscope that comprises an internal magnetic field and provides acceleration data, wherein the magnetic field data is obtained according to the external magnetic field and the internal magnetic field; and
a data processing device that obtains the orientation information of the capsule endoscope according to the acceleration data and the magnetic field data, wherein
when a polarization direction of the external magnetic field is horizontal, the data processing device obtains the orientation information of the capsule endoscope according to the acceleration data; and
when the polarization direction of the external magnetic field is non-horizontal, the data processing device obtains the orientation information of the capsule endoscope according to the acceleration data and the magnetic field data,
wherein the capsule endoscope system is configured to obtain orientation information of the capsule endoscope by
obtaining a tilt angle of the capsule endoscope to ground according to the acceleration data;
obtaining a distance between the external magnet and the capsule endoscope and a vector angle between a direction vector of the external magnet and a direction vector of the capsule endoscope according to the magnetic field data;
obtaining a magnetic field direction of the external magnet in a geodetic coordinate system according to the distance;
obtaining the orientation information of the capsule endoscope according to the tilt angle of the capsule endoscope to ground, the vector angle and the magnetic field direction.

9. The system of claim 8, wherein the capsule endoscope comprises:
an internal magnet that provides an internal magnetic field;
an acceleration sensor that obtains an acceleration value of the capsule endoscope;
a magnetic field sensor that obtains a magnetic field value according to the internal magnetic field and the external magnetic field; and
a microprocessor that obtains the acceleration data according to the acceleration value, and obtain the magnetic field data according to the magnetic field value.

10. The system of claim 9, wherein the polarization direction of the internal magnet is along a direction of a long axis of the capsule endoscope.

11. The system of claim 9, wherein a z-axis of the acceleration sensor, a z-axis of the magnetic field sensor, and a long axis of the internal magnet coincide with the long axis of the capsule endoscope.

12. The system of claim 9, wherein the capsule endoscope further comprises an antenna module for radiating radio frequency signals representing the acceleration data and the magnetic field data.

13. The system of claim 8, further comprising:
a three-dimensional energized coil that detects a position coordinates of the capsule endoscope.

* * * * *